United States Patent
Lipton (12)

(10) Patent No.: US 6,525,017 B1
(45) Date of Patent: Feb. 25, 2003

(54) USING GLUTATHIANE TO PROTECT NEURONS FROM INJURY

(75) Inventor: Stuart A. Lipton, Newton, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 08/245,827

(22) Filed: May 19, 1994

Related U.S. Application Data

(63) Continuation of application No. 08/009,376, filed on Jan. 27, 1993, now abandoned, which is a continuation of application No. 07/730,587, filed on Jul. 15, 1991, now abandoned, which is a continuation of application No. 07/391,778, filed on Aug. 9, 1989, now abandoned.

(51) Int. Cl.[7] ........................ A61K 38/00; A61K 38/06
(52) U.S. Cl. ............................................. 514/2; 514/19
(58) Field of Search ................................ 435/5, 15, 25, 435/29, 30; 436/501, 811; 514/485, 506, 646, 678, 464, 18, 19, 17; 530/358, 399, 839, 331

(56) References Cited

U.S. PATENT DOCUMENTS 4,871,528 A * 10/1989 Tognella et al. .............. 424/10

FOREIGN PATENT DOCUMENTS

WO    WO 88/05306    7/1988

OTHER PUBLICATIONS

Jackowski, British J. of Neurosurgery 9(1995) 303–317.*
Lehninger In "Biochemistry" (1975), Record Edition, Worth Publishers Inc. N.Y. N.Y. p. 795.*
De Ryck European Neurol. 30(Suppl. 2): 21–27 (1990).*
Hahn Et Al. (1988) Proc. Nat'l Acad Sci (USA), vol. 85, pp 6556–6560.*
Simon et al., Ann. Rev. Pharmacol. Toxicol. 18:371–94 (1978).
Ogita et al., Neuroscience Res. 4:485–496 (1987).
Majewska et al., Society For Neuroscience Abstracts, vol. 15, p. 1167, No. 463.15 (1989).
Aizenman et al., Neuron 2:1257–1263 (1989).
Karlin et al., Biochem. Biophys. Acta 126:525–535 (1966).
Aronstam et al., Mol. Pharmacol. 14:575–586 (1978).
Simon et al., Ann. Rev. Pharmacol. Toxicol. 18:371–394 (1978).
Kiskin et al., Neurosci Lett. 66:305–310 (1986).
Braestrup et al., J. Neurochem. 48:1667–1672 (1987).
Terramani et al., Mol. Pharmacol. 34:117–123 (1988).
Loring et al., J. Neurosci. 9:2423–2431 (1989).

* cited by examiner

*Primary Examiner*—Gary Kunz
*Assistant Examiner*—Robert Hayes
(74) *Attorney, Agent, or Firm*—Fish & Richardson P.C.

(57) ABSTRACT

A method for identifying agents useful for protection of a human neuron from injury. The method includes the steps of providing a cell which has NMDA receptor; selecting a agent potentially useful for oxidation of the NMDA receptor; treating the cell with the agent; and determining whether the NMDA receptor is oxidized by the agent.

4 Claims, No Drawings

USING GLUTATHIANE TO PROTECT NEURONS FROM INJURY

This application is a continuation of U.S. Ser. No. 08/009,376, filed Jan. 27, 1993, now abandoned, which in turn was a continuation of U.S. Ser. No. 07/730,587, filed Jul. 15, 1991, now abandoned, which is in turn a continuation of U.S. Ser. No. 07/391,778, filed Aug. 9, 1989, now abandoned.

This invention was made with U.S. Government support in the form of grants from the NIH, numbers EY05477 and N900879. The U.S. Government has certain rights in the invention.

BACKGROUND OF THE INVENTION

This invention concerns agents, and methods of their use, which protect a neuron of a human patient from injury, especially injury caused by the presence of excess glutamate or related compounds.

Glutamate is known to be a broad spectrum agonist of neuron activity, with efficacy at at least three subtypes of excitatory amino acid receptors, namely kainate, quisqualate, and N-methyl-D-aspartate (NMDA). It is present at high concentrations in mammalian central nervous systems (CNS) and is toxic to central neurons. It is thought to play a role in neuronal injury, and to mediate a variety of brain insults, including hypoxia, physical trauma, and Alzheimer's disease.

Certain glutamate antagonists can attenuate the acute neuronal injury produced by hypoxia, ischemia, and hypoglycemia. This protective effect on central neurons indicates that the antagonists may have clinical therapeutic utility in hypoxic brain injury. Choi, U.S. Pat. No. 4,806,543, describes a method for reducing adverse effects of neurotoxic injury by administering an enantiomer of an analgesic opioid agonist or antagonist. Such compounds are said to be useful for treatment of any animal species having NMDA receptors.

Hahn et al. (Proceedings National Academy of Science USA, 85:6556, 1988; not admitted to be prior art to the present invention) state that, in the mammalian central nervous system, glutamate is thought to be the major excitatory neurotransmitter that acts at the three receptor subtypes. Excessive stimulation of the NMDA subtype has been implicated in the pathophysiology of neuronal degeneration caused by a variety of conditions; these include anoxia, ischemia, hypoglycemia, seizures, and several neurodegenerative diseases, such as Huntington's disease, and the amyotrophic lateral sclerosis-Parkinsonism-dementia complex found on Guam.

SUMMARY OF THE INVENTION

In a first aspect, the invention features a method for identifying agents useful for protection of a neuron of an organism from injury. The method includes the steps of providing a cell which has an NMDA receptor; selecting an agent potentially useful for oxidation of the NMDA receptor; treating the cell with the agent; and determining whether the NMDA receptor is oxidized by the agent.

By protection of a neuron from neuronal injury is meant that the agent is able to either totally reverse, or at least partially reverse, the effect of excess glutamate on that neuron. Alternatively, the agent is able to reduce the effect of glutamate on the neuron, and thereby significantly increase the chances of that neuron surviving in the presence of glutamate or a related substance.

The term organism is intended to include any animal to which an agent of the invention can be administered for the indicated purpose, including both medicinal and veterinary purposes. Use in mammals and birds of all types is preferred, with use in humans being a primary utility.

The NMDA receptor is that molecule found in human neurons which interacts with NMDA to induce neuron excitation. Cells which include an NMDA receptor include any cell which has an NMDA receptor analogous to that present on human neurons in the CNS. Generally such cells are neurons and can be isolated from any organism, including humans. Examples of such cells include rat retinal ganglion cells, cultured mammalian central neurons, such as rat cortical neurons, cells of an intact chick retina, and glial cells.

The step of selecting an agent potentially useful for oxidation of the NMDA receptor is a step well understood by those skilled in the art. Generally, this step involves choosing any agent which is able to act as an oxidizing agent, and thus may act as such at the NMDA site. One example of an agent useful in the invention is DTNB (generally used in vitro at 0.5–10 mM). The agent is generally used in vivo, thus the agents screened generally will be those which have minimal adverse side effects on the organism to which they are to be administered. Those skilled in the art will readily recognize the meaning of this phrase, but generally it indicates that the effect of adding the agent to an organism to protect a neuron from injury causes minimal other effects to that organism, such as cell death, disruption of other physiological functions, and gross comfort of the organism. Preferably, agents useful in this invention will have little, if any, side effects on the organism to which they are administered.

Useful agents need not be oxidizing agents in their own right, and include those agents which will be acted upon in vivo to produce oxidizing agents at the in vivo site of the NMDA receptor which is to be protected from neuronal injury. Thus, a substrate for an enzyme naturally occuring within the organism, or separately provided, which is acted upon by that enzyme to produce a product which acts as an oxidizing agent for the NMDA receptor is useful in this invention. Indeed, if the product itself is not an oxidizing agent, but can be subsequently acted upon by another enzyme to produce an oxidizing agent, it is also useful in this invention. It is understood by those of ordinary skill in the art that such agents, which are not themselves oxidizing agents, are only useful if the enzymes or other compounds which must preferably act upon the administered agent naturally occur within the organism in close proximity to the NMDA receptor. For example, agents such as superoxides and peroxides are potentially useful as agents to oxidize an NMDA receptor in vivo. Thus, putrescene, the substrate for diamine oxidase, is a useful agent in this invention since it will cause production of peroxides which may oxidize an NMDA receptor. Other examples of agents which are potentially useful for oxidation of an NMDA receptor include substrates of xanthine oxidase (e.g., xanthine-ring containing substances), amino acid oxidases (e.g., D-serine, the substrate for a D-amino acid oxidase), lysine oxidase, monoamine oxidase (e.g., dopa may be used to generate peroxide in the CNS after it crosses the blood-brain barrier, is metabolized to dopamine, and is later acted upon by monoamine oxidase to generate peroxide), tyramine-containing foods or drugs, and other agents which may generate catecholamines in the CNS.

As discussed above, it is readily apparent to those skilled in the art how to select agents potentially useful for oxidation of the NMDA receptor. However, it must be noted that, in the method of this invention, the step of treating the cell with the agent means provision of the agent along with any of the enzymes or other products necessary to produce the oxidizing agent which will act in vivo on the NMDA receptor. For example, if putrescene is to be used in the method of the invention, both putrescene and diamine oxidase must be provided at the treating step. Alternatively, the product of such a combination, which is produced in vivo, for example, hydrogen peroxide, can be tested by the method of the invention and, if found to oxidize an NMDA receptor, that agent may be produced in any manner suitable in vivo. Thus, if hydrogen peroxide in low dose (e.g., maximally at 25 $\mu$M, or between 2.5 and 20 $\mu$M) is determined to be a suitable agent for protection of neurons, the hydrogen peroxide may be produced in vivo by any manner of known techniques, for example, by direct administration of hydrogen peroxide, or by use of the substrate-enzyme combinations discussed above.

Other agents which may be selected for testing in the method of this invention include those which prevent removal of oxidizing agents which occur naturally in vivo. For example, agents which prevent removal or destruction of superoxides and peroxides generated in vivo will result in a higher in vivo concentration of these superoxides or peroxides, thus causing greater oxidation of the NMDA receptor. Those skilled in the art will readily recognize that one example of such agents includes inhibitors of enzymes known to break down these oxidizing compounds. Such inhibitors must be chosen and used at concentrations which do not allow too great a level of superoxide or peroxide to accumulate in the CNS, which may be toxic to the neurons. The usefulness of these agents is determined by performing the above method in the presence of compounds which naturally break down useful naturally-occurring oxidizing compounds. For example, an inhibitor of a peroxidase is tested in the presence of a naturally occurring peroxidase and a peroxide.

To determine whether the NMDA receptor is oxidized by the agent in the method, any number of methods may be used. For example, it is possible to measure the electrophysiological response of the cell to NMDA, and to determine the survival of the cell after exposure to the agent in the presence or absence of glutamate. Survival can be measured by any of a number of techniques, examples of which are presented below.

The method of this invention is suitable for identifying oxidizing agents which decrease, at least temporarily, NMDA receptor activity in vivo, and thus protect a neuron from neuronal injury. The identified agents are useful for treatment of neurological illness including strokes, anoxia, and the degenerative diseases discussed above. Modulation of the NMDA site by these agents allows central neurons to be protected from death or injury caused by activation of the NMDA subtype of the glutamate receptor. The agents are also useful for in vitro treatment of neurons to increase their longevity, and reduce chances of death.

In a second aspect, the invention features a method for protecting a neuron of an organism from neuronal injury. The method includes identifying an organism susceptible to neuronal injury, providing a pharmacologically acceptable composition including an agent which causes oxidation of an NMDA receptor, and administering the agent to the organism in an amount sufficient to oxidize an NMDA receptor.

Organisms, e.g., human patients, susceptible to neuronal injury are identified by any of a number standard techniques. Such patients will include those discussed above which are susceptible to, or suffer from, strokes, anoxia and certain degenerative diseases. They will also include those patients which have no symptoms but are found to have abnormally high levels of glutamate or related compounds in the CNS. The agents which are identified by the method described above, or by any other method, may be used for treatment of these patients. Those skilled in the art will recognize how to determine, by routine experimentation, the amount of agent necessary to provide sufficient oxidation of NMDA receptors without causing significant deleterious or side effects to the patient. Generally, this amount will be a balance between a level of agent where the potential of causing such deleterious effects is significant and a level where the agent provides complete protection against injury to the NMDA receptor.

In a third aspect the invention features a pharmacologically acceptable therapeutic composition, which includes any one of the above agents which cause oxidation of the NMDA receptor, admixed in a buffer to allow administration of the composition to an organism.

By "causes oxidation" of an NMDA receptor is meant to include agents which directly cause oxidation of the NMDA receptor, as well as agents which cause the in vivo level of an oxidizing agent of NMDA receptor to be increased.

Applicants have discovered that oxidation of the NMDA receptor by oxidizing agents provides protection of neurons from injury caused by the effect of glutamate on that receptor. Thus, these agents can be used to protect neurons which have NMDA receptors in vivo, and specifically those present in the CNS of a human. These agents are particularly useful for treatment of humans suffering from strokes, anoxia or certain degenerative diseases.

Applicants have also discovered that both reduced and oxidized glutathione (0.5–10 mM) can protect against toxicity mediated at NMDA receptors by a mechanism not related to the site of oxidation discussed above. Thus glutathione can be used in vivo or in vitro as discussed in this application for those agents which act to oxidize the NMDA receptor.

Other features and advantages of the invention will be apparent from the following description of the preferred embodiments thereof, and from the claims.

DESCRIPTION OF THE PREFERRED EMBODIMENTS

The following are examples of methods by which agents may be identified which are useful for in vivo protection of neurons from neuronal injury. These examples include examples of the methods of use of these agents. In these examples the oxidizing agent 5'-5'-dithiobis-2-nitrobenzoic acid (DTNB) is used as an oxidizing agent. This agent is used only as an example of how an oxidizing agent may be tested in the methods of the invention. DTNB itself is not useful for in vivo treatment of organisms because it may have significant deleterious effects on a patient. However, those skilled in the art will readily recognize that agents which are suitable for use in the methods described below, and are of use for in vivo protection of neurons, can be simply substituted for DTNB in the methods described below.

The following three examples (Examples 1–3) are described in Aizenman et al. Neuron 2:1257, 1989, the whole of which is hereby incorporated by reference herein.

EXAMPLE 1

Effect of DTNB on Chick Retinas

The effects of dithothreitol (DTT) and DTNB on NMDA-induced responses were first observed in recordings of intact chick retinas.

Eyecups were obtained from 2-to 5-day-old chicks and continuously superfused at 20–25° C. at a rate of 8 ml/min with Tyrodes solution (130 mM NaCl, 3 mM KCl, 17 mM dextrose, 20 mM $NaHCO_3$, 0.01% w/v phenol red; bubbled with a gas mixture of 95% $O_2$ and 5% $CO_2$) containing 5 mM $MgCl_2$ to reduce synaptic activity. The DC potential between a unipolar suction electrode placed on the cut optic nerve and a unipolar $Ag^+$/AgCl electrode placed inside the eyecup solution was amplified 1000× and displayed on an oscilloscope. Traces were triggered by the opening of two solenoid valves that shunted approximately 200 μl of agonist (1, 1-dimethyl-4-phenyl-piperazinium iodide, DMPP or NMDA) into the perfusion line, Agonists reached the preparation approximately 7s later. The resulting responses originated, at least in part, in the retinal ganglion cells. Some experiments were performed in the presence of 10 μg/ml catalase and 1 μg/ml superoxide dismutase. Antagonists, reducing agents, or oxidizing agents were introduced directly via the perfusate.

Treatment with the disulfide-reducing agent DTT (1–2 mM applied for 10–25 min) blocks nicotinic receptor function in the intact chick retina. Surprisingly, DTT was observed to potentiate the response to 100 μM NMDA substantially in this preparation (530%±280% of control; range, 200%–860%). The NMDA receptor competitive antagonist 2-amino-5-phosphonovalerate (APV; 100 μM) blocked NMDA-induced responses in both the native and the reduced states. The action of DTT lasted for tens of minutes after the reducing agent was removed; any small decrement in the potentiation could be reversed with additional DTT treatment. The function of the nicotinic receptors was restored upon oxidation with 0.1–1.0 mM DTNB (applied for 5 min). However, the NMDA response following oxidation was either substantially diminished compared with controls or completely abolished (81.6%±24.1% decrease; range, 43%–100%). The reduction and oxidation effects could be alternated repeatedly for as long as the preparation remained stable, which was often more than 9 hr.

In contrast to the action on either nicotinic or NMDA responses, reduction or oxidation (regardless of order) had no effect on responses elicited by other classes of excitatory amino acid analogs (100 μM each), such as kainate, quisqualate, or 3-hydroxy-5-methylisoxazole-4-propionate (AMPA).

EXAMPLE 2

Effect of DTNB on Central Neurons

The effects of reduction and oxidation on the NMDA response were further examined in cultured mammalian central neurons with the use of patch electrodes. Experiments were performed on neurons in primary cultures of CD rat neocortex derived from embryonic day 16 fetuses and plated onto glass coverslips coated with collagen and poly-L-lysine. The growth medium consisted of a v/v mixture of 80% DMEM (Sigma D5530), 10% F-12 (Sigma), 10% heat-inactivated, iron-supplemented serum (Hyclone), with 25 mM HEPES, 24 U/ml penicillin, and 24 μg/ml streptomycin, supplemented to 2 mM glutamine. Recordings were made on 3- to 13-week-old cultures, and neurons studied ranged from 12 to 18 μm in diameter. The extracellular solution for the physiological experiments contained 137 mM NaCl, 1 mM $NaHCO_3$, 0.34 mM $NaHPO_4$, 5.36 mM KCl, 0.44 mM $KH_2PO_4$, 2.5 mM $CaCl_2$, 5 mM HEPES-NaOH, 22.2 mM dextrose, 0.001% (v/v) phenol red, adjusted to pH 7.2 with 0.3 N NaOH (no added magnesium, except where noted). Tetrodotoxin (TTX) (1 μM) was routinely added to reduce synaptic activity. The intracellular (pipette) solution contained 120 mM CsCl, 20 mM TEA-Cl, 2 mM $MgCl_2$, 1 mM $CaCl_2$, 1.5–2.25 mM EGTA, and 10 mM HEPES-NAOH, adjusted to pH 7.2 with concentrated TEA-OH. Electrophysiological measurements were performed at 33° C.–35° C. with patch electrodes (4–8 MΩ), essentially as described in Lipton et al. J. Physiol 385:361, 1987. Lipton et al. 1987 includes the following disclosure of electrophysiological recordings by patch clamp from solitary neurons:

"... patch-clamp recordings were made ... following the methods of Hamill et al. (1981) using an EPC-7 amplifier (List Electronic, Darmstadt, F.R.G.). Patch electrodes had resistances of 3–5 MΩ when filled with $Na^+$ or $K^+$ saline. Patch electrodes were used to record whole-cell currents under voltage clamp as well as single-channel currents from patches of membrane excised from the cell. The indifferent electrode was a Ag-AgCl wire connected to the culture dish via an agarose bridge. Holding and command potentials ($V_H$ and $V_c$, respectively (were generated by a digital-to-analog converter (Cheshire Data, Hamden, Conn., U.S.A.) interfaced with a PDP 11/23 or 11/73 computer (Digital Equipment Corp., Maynard, Mass., U.S.A.). Data collection was also controlled by the computer; data were sampled and digitized with a 12-bit, 125 kHz analog-to-digital converter (Data Translation, Marlboro, Mass., U.S.A., Model DT2782DMA) and viewed on a Hewlett-Packard digital display (Model 1345A). The sampling rate was set at 10 μs to 50 ms depending on the level of analysis. Using the amplifier test circuit, the digitized data were accurate to within 1%. The signals were low-pass filtered at a setting appropriate to the sampling frequency (Ithaco, Ithaca, N.Y., U.S.A., Model 4302 with a Bessel frequency cut-off characteristic of 48 dB/octave). Leakage currents and liquid junction potentials were corrected as described in Fenwick, Marty & Neher [J. Physiol. 331:577–597] (1982a). Using the EPC-7 circuit, analog compensation of the series resistance was applied. This ensured a relatively small error due to the voltage drop across the series resistance (less than or equal to that calculated by Marty & Neher, 1985 [J. Physiol. 367:117–141]). Data were stored on a 30 megabyte Winchester disk (Data Systems Design, San Jose, Calif., U.S.A., Model 880). For long-term storage data files were transferred to a streaming tape (Alloy Computer Products, Marlborough, Mass., U.S.A., Model LSI-50). Cortical neurons had an input resistance of 0.1–1.0 GΩ and a cell capacitance of 6–30 pF. Agonists were applied by pressure ejection from micropipettes (5 μm aperture) placed in close proximity (20 μm) to the cell under study. DTT and DTNB were applied via a superfusion system that continuously bathed the cells at a rate of 0.8 ml/min.

NMDA responses recorded from rat cortical neurons in culture under the whole-cell recording configuration (Hamill et al., Pflugers Arch. 391:85, 1981) were observed to behave in a fashion similar to the isolated chick retina after treatment with either DTT or DTNB. Voltage-clamped responses elicited by a combination of 10–100 μM NMDA and 1 μM glycine, in either the presence or the absence of extracellular magnesium, were observed to be substantially potentiated after a 1–5 min treatment with 0.5–2.0 mM DTT (250%±140% of control; range, 220%–330%; n=7). In contrast, either prior to or following reduction, a 1–3 min treatment with 0.1–1.0 mM DTNB rendered the NMDA responses comparable in size to those seen in the native state or diminished them to less than control levels (22.9%±12.9% decrease; range, 0%–39.5%). Reapplication of DTT after oxidation always restored the NMDA response to greater than control levels. In general, the response in the native state was more similar to the response observed after DTNB treatment than that observed after DTT treatment. This finding suggests that the sites responsible for this phenomenon in cortical neurons in vitro exist in a more oxidized than reduced state. Also, in this preparation the oxidation and reduction treatments could be altered repeatedly as long as the recording remained stable.

Peak currents induced by NMDA and glycine in cortical neurons were measured at various holding potentials after treatment with both DTT and DTNB in the absence of extracellular magnesium. This procedure generated current-voltage relations in which the effects of oxidation and reduction are observed to occur at all physiological potentials (−60 to +40 mV).

EXAMPLE 3

Effect of DTNB on Retinal Ganglion Cells

The third central neuronal preparation in which the effects of oxidation and reduction on NMDA responses were tested was the isolated rat retinal ganglion cell. Postnatal retinal ganglion cells were identified and cultured as described in Lipton et al., supra. Physiological solutions and experimental protocol were the same as described for cortical neurons (Example 2), except that TTX was excluded from the extracellular fluid, since whole-cell recordings were performed on neurons that were solitary and had no apparent connections to other cells and no spontaneous action potentials. Retinal ganglion cells were utilized after 12–30 hr in culture and had an input resistance of 1.4–11.0 GΩ and a cell capacitance of 5–13 pF.

These cells have well-characterized, albeit small, NMDA responses. Treatment with 2 mM DTT (1–3 min) produced potentiation of the response elicited by 200 $\mu$M NMDA and 1 $\mu$M glycine (250%±130% of control; range, 220%–320%). In this preparation, application of 0.1–0.2 mM DTNB also produced a decrement of the native response (49.4%±9.4% decrease; range 37%–60%). Glycine (1 $\mu$M) potentiation of NMDA (200 $\mu$M) responses occurred in both the reduced and the oxidized states. Interestingly, in some of the retinal ganglion cells tested, we observed a small degree of potentiation by DTT from the native state when compared with the decrement generated by DTNB. Once again, this finding suggests a variability in the redox state of the native site that is susceptible to reduction and oxidation. The effects of reduction and oxidation could be repeated in alternating fashion in these cells for as long as the recording remained stable.

In the retinal ganglion cells, we further tested the effects of DTT and DTNB on responses elicited by glutamate analogs acting at non-NMDA receptors to confirm our previous observations in the chick retina, i.e., a lack of effect of reduction and oxidation on responses induced by agonists acting at non-NMDA receptors. Reduction with 1 mM DTT produced no substantial effect on currents elicited by either 125 $\mu$M kainate, 60 $\mu$M AMPA, or 30 $\mu$M quisqualate. In addition, oxidation with 200 $\mu$M DTNB did not affect the responses elicited by these three agonists.

EXAMPLE 4

Effect on DTNB on Survival of Retinal Ganglion Cells

To investigate the influence of redox modulation on NMDA neurotoxicity, survival of an identified central neuron, the retinal ganglion cell, was monitored for 12–24 hr after a brief (5–10 min.) exposure to DTT. To determine the degree of killing specifically related to activation of the NMDA receptor, APV at 200 $\mu$M was added to sibling cultures. APV-preventable, glutamate-induced death was increased 70±9% with DTT treatment. This effect was totally blocked by the concomitant addition of DTNB. These findings suggest that the enhanced killing following chemical reduction with DTT is mediated at the NMDA receptor site, and that the redox state of the NMDA receptor is crucial for the survival of neurons facing glutamate-related injury. These results were obtained as follows.

Retinal ganglion cell neurons were labeled in situ, dissociated from the retina, and cultured as follows. Retinal ganglion cells from 7- to 12-day-old Long-Evans rats were labeled and enzymatically dissociated as described by Leifer et al., Science 224: 303, 1984. Following rinse of the dissociated retinal cells with a physiological saline based on Hanks' salts (composition in mM: NaCl, 137; NaHCO$_3$, 1; Na$_2$HPO$_4$, 0.34; KCl, 5,36; KH$_2$PO$_4$, 0.44; CaCl$_2$, 1.25, MgSO$_4$, 0.5; MgCl$_2$, 0.5; N-2-hydroxyethyl-piperazine-N'-2-ethanesulfonic acid (HEPES), 5; dextrose, 22.2; Phenol Red, 0.001% v/v; adjusted to pH 7.2 with 0.3 M NaOH), the cells were mechanically dispersed and aliquoted to treatment vials. These vials contained control saline solution, or saline solution with either 0.5–2 mM DTT, or 0.5 mM DTT in the presence of 1 mM DTNB. Treatment groups with DTNB were readjusted to pH 7.2 with 0.3 M NaOH. Cells were agitated gently over a 5–10 min period. After treatment, 100 $\mu$l volumes of the cell suspension were plated onto glass coverslips coated with poly-L-lysine in 35×10 mm tissue-culture dishes containing 2 ml of culture medium. The cell culture medium was based on Eagle's minimum essential medium (MEM), modified so that it was nominally free of magnesium and contained 10 mM CaCl$_2$ to enhance NMDA receptor-mediated neuro-toxicity. The medium was also supplemented with methylcellulose 0.7% w/v, gentamicin 1 $\mu$g/ml, dextrose 16 mM, and rat serum 5% v/v. Glutamate levels in the culture medium were monitored by HPLC analysis. Concentrations of glutamate added to the medium of each experiment to induce cell killing averaged 10 $\mu$M (day to day variability in neuronal cell death was most probably due to slight variations in the amount of endogenous glutamate or a glutamate-like substance in these cultures). The 100 $\mu$l aliquots of cell suspension diluted into the 2 ml of MEM produced a final concentration of 50 $\mu$M Mg$^{2+}$, as well as levels of DTT and DTNB at 5% of their initial treatment concentrations. The cell cultures were incubated for 12–24 hours at 37° C. in an atmosphere of 5% CO$_2$/95% humidified air. Neuronal survival was then scored by counting retinal ganglion cells displaying uptake and cleavage of fluorescein diacetate to fluorescein, as described by Hahn et al. Proc. Nat. Acad. Sci. USA 85:6556, 1988.

Experiments were conducted in triplicate and repeated on eleven separate days. In order to compare results obtained on different days, data were normalized such that the total number of surviving neurons in a given experiment divided by the number of treatment categories (i.e., 4) equalled 100. Each of the treatment categories was significantly different from baseline susceptibility (P<0.01) by an analysis of variance followed by a Scheffe multiple comparison of means performed on the raw data or on the pooled data. APV (200 $\mu$M) prevented the death of retinal ganglion cells exposed to glutamate in the culture medium. On the other hand, transient exposure to DTT substantially increased death. Vulnerability of the neurons could be blocked with 200 $\mu$M APV despite DTT treatment. This finding strongly suggests that the increased susceptibility of neurons following treatment with the reducing agent was mediated via the NMDA receptor.

Unlike the reduced form, oxidized dithiotheritol (DTT) does not significantly affect NMDA receptor-mediated neurotoxicity. Retinal cells were cultured as described in Example 1. In these experiments transient exposure to the reduced form of DTT (500 μM) occurred in the presence of DTNB (1 mM). The experiments were conducted in triplicate and repeated on four separate days; survival in cultures treated with APV was significantly greater than baseline by an analysis of variance followed by a Scheffe multiple comparison of means (P<0.01). In contrast, exposure to the combination of DTT/DTNB did not affect neuronal survival compared to baseline.

In contrast to the findings obtained with the reduced form of DTT, oxidized DTT does not effect neuronal cell injury. Oxidized DTT was produced from the reduced form using the oxidizing agent DTNB and following the chemical conversion spectrophoto-metrically. Spectrophotometric analysis of the redox state reduced DTNB is highly colored (maximum absorbance =412 nm). Thus, the reduced form of DTNB can be assayed to quantify the level of a complementary reducing agent (Ellman, Arch. of Biochem. Biophys. 82: 70, 1959). In this manner it was found that mixing reduced DTT with oxidized DTNB in a 1:2 ratio resulted in the oxidation of greater than 90% of the DTT, virtually eliminating its reductive capacity.

The above examples are not limiting to the present invention. They are only meant as examples of methods which can be used to identify agents useful for treatment of diseases caused by an excess amount of endogenous excitatory amino acids, such as glutamate and/or the related endogenous compounds quinolinate, homocysteate, and asparate. For example, another method for assay of neuronal injury includes the assay described by Choi, U.S. Pat. No. 4,806,543, which is hereby incorporated by reference. This assay includes measuring the extracellular concentration of the cytosolic enzyme lactate dehydrogenase (LDH) released to the culture medium by damaged neurons. Spontaneous release of LDH is generally low unless injury to a neuron occurs. Agents useful in the invention will maintain the level of LDH at this low level even in the presence of glutamate.

The methods of this invention are useful for identification of agents useful in treatment of central neuronal injury, such as the acute and chronic neurological diseases of ischemia, hypoxia, hypoglycemia, epilepsy, Huntington's disease, and Alzheimer's disease. These agents act to selectably block the neurotoxicity of glutamate at only one of the glutamate receptors, namely the NMDA receptor, and thus allow accomplishment of protection against glutamate with a low number of side effects. Thus, there is less disruption of normal brain function by these agents than by compounds effective at more than one site. It is, of course, possible to use the agents identified above in conjunction with other compounds which act at other sites of the NMDA subclasses of glutamate receptors. In fact, such use will provide synergistic results, in that the level of protection of the neuron from neuronal injury will be greater than the protection provided by either agent alone. This means that lower levels of agents, which are identified as useful in the invention can be used in combination with agents which act at other sites. Thus, advantageous compositions useful for treatment of the above diseases can be formed by combinations of existing agents, and those identified by the method of the present invention.

Agents identified by the above methods can be used by standard procedures in treatment of the above mentioned diseases, and related diseases or symptoms. These agents are administered to patients susceptible to neuronal injury in an amount of an agent sufficient to reduce the neuronal injury. Such administration can be performed on any animal having an NMDA receptor and includes mammals, birds and, in particular, humans.

Administration can be by any technique capable of introducing the agent into the blood stream of the patient, and preferably through the blood-brain barrier. These techniques include oral administration, and intravenous, intramuscular, and subcutaneous injections.

The agents of the invention can be formulated into orally administerable forms or pills by standard procedure. Typical doses of the agents in pharmaceutically acceptable carriers would be from 50 mg to 2 g and preferably from 100 mg to 1 g. These doses are suitable for administration to a typical 70 kg human. Administration can be adjusted to provide the same relative dose per unit of body weight. Typically useful concentrations of the agents in the blood stream will be in the order of 1 to 1000 micromolar, preferably from 1 to 100 micromolar, even more preferably 2.5 to 25 micromolar.

Other embodiments are within the following claims.

What is claimed is:

1. A method for treating a human patient to limit NMDA receptor-mediated injury to CNS neurons by providing a pharmacologically acceptable composition comprising glutathione and administering said composition to said patient in an amount sufficient to limit said neuronal injury.

2. A method of treating a patient to limit neuronal injury associated with stroke by administering to the patient a pharmacologically acceptable composition comprising glutathione and administering said composition to said patient in an amount sufficient to limit neuronal injury associated with stroke.

3. A method of treating a patient to limit neuronal injury associated with central nervous system ischemia by administering to the patient a pharmacologically acceptable composition comprising glutathione and administering said composition to said patient in an amount sufficient to limit neuronal injury associated with ischemia.

4. The method of claim 1, 2, or 3 in which the glutathione comprises glutathione in reduced form.

* * * * *

UNITED STATES PATENT AND TRADEMARK OFFICE
CERTIFICATE OF CORRECTION

PATENT NO. : 6,525,017 B1
DATED : February 25, 2003
INVENTOR(S) : Stuart A. Lipton It is certified that error appears in the above-identified patent and that said Letters Patent is hereby corrected as shown below:

Title page, Item [54] and Column 1, line 1,
Title, "GLUTATHIANE" should be -- GLUTATHIONE --.

Signed and Sealed this

Twenty-fourth Day of January, 2006

JON W. DUDAS
*Director of the United States Patent and Trademark Office*